(12) United States Patent
Smith

(10) Patent No.: US 9,666,052 B1
(45) Date of Patent: May 30, 2017

(54) PORTABLE ENVIRONMENT MONITORING AND EARLY WARNING SYSTEM FOR BABIES

(71) Applicant: Elliot John Smith, Boulder, CO (US)

(72) Inventor: Elliot John Smith, Boulder, CO (US)

( * ) Notice: Subject to any disclaimer, the term of this patent is extended or adjusted under 35 U.S.C. 154(b) by 0 days.

(21) Appl. No.: 14/595,198

(22) Filed: Jan. 12, 2015

Related U.S. Application Data

(60) Provisional application No. 61/926,342, filed on Jan. 12, 2014, provisional application No. 62/062,560, filed on Oct. 10, 2014.

(51) Int. Cl.
*G08B 23/00* (2006.01)
*G08B 21/02* (2006.01)
*G08B 21/18* (2006.01)

(52) U.S. Cl.
CPC ....... *G08B 21/0236* (2013.01); *G08B 21/182* (2013.01)

(58) Field of Classification Search
None
See application file for complete search history.

(56) References Cited

U.S. PATENT DOCUMENTS

| | | | |
|---|---|---|---|
| 5,033,864 A | 7/1991 | Lasecki et al. | |
| 6,995,665 B2 | 2/2006 | Appelt | |
| 7,397,380 B1 | 7/2008 | Smolsky | |
| 7,425,901 B2 * | 9/2008 | Groover | G08B 21/0208 340/539.15 |
| 7,482,935 B2 | 1/2009 | Lee | |
| 7,973,665 B2 | 7/2011 | Desrosiers | |
| 8,050,631 B2 | 11/2011 | Gross | |
| 8,085,145 B2 | 12/2011 | Fu et al. | |
| 8,314,696 B2 | 11/2012 | Stut | |
| 8,663,106 B2 * | 3/2014 | Stivoric | G06F 19/3418 374/164 |
| 8,716,629 B2 | 5/2014 | Klewer et al. | |
| 8,967,855 B1 | 3/2015 | Joshi et al. | |
| 2005/0001728 A1 * | 1/2005 | Appelt | G08B 21/182 340/573.1 |
| 2005/0088296 A1 * | 4/2005 | Lee | G08B 21/02 340/539.12 |
| 2010/0241018 A1 | 9/2010 | Vogel | |

(Continued)

FOREIGN PATENT DOCUMENTS

| | | |
|---|---|---|
| CA | 2560323 | 10/2005 |
| WO | WO0026882 | 5/2000 |
| WO | WO2012170177 | 12/2012 |

*Primary Examiner* — Julie Lieu
(74) *Attorney, Agent, or Firm* — Furman IP Law

(57) ABSTRACT

The present disclosure describes an apparatus and method for monitoring the environment of a baby, i.e. the outside environment and the direct environment in direct contact with the baby. Environment elements which can be monitored include the temperature, humidity, sunlight intensity and whether or not the environment is damp. Using the temperature and humidity data, the heat index can also be calculated. The child's direct environment is a weighted value which considers the environment elements relating directly to the child and the direct ambient surroundings of the child. This weighted value, for instance, takes into account the skin temperature of the child as well as the ambient temperature, humidity, dampness of the direct surroundings of the child.

3 Claims, 15 Drawing Sheets

(56) References Cited

U.S. PATENT DOCUMENTS

| | | |
|---|---|---|
| 2011/0265706 A1 | 11/2011 | Nicholls |
| 2012/0197584 A1 | 8/2012 | Coates |
| 2013/0254141 A1* | 9/2013 | Barda ................. A61F 13/42 706/12 |
| 2015/0094914 A1* | 4/2015 | Abreu ............... B60H 1/00742 701/41 |

* cited by examiner

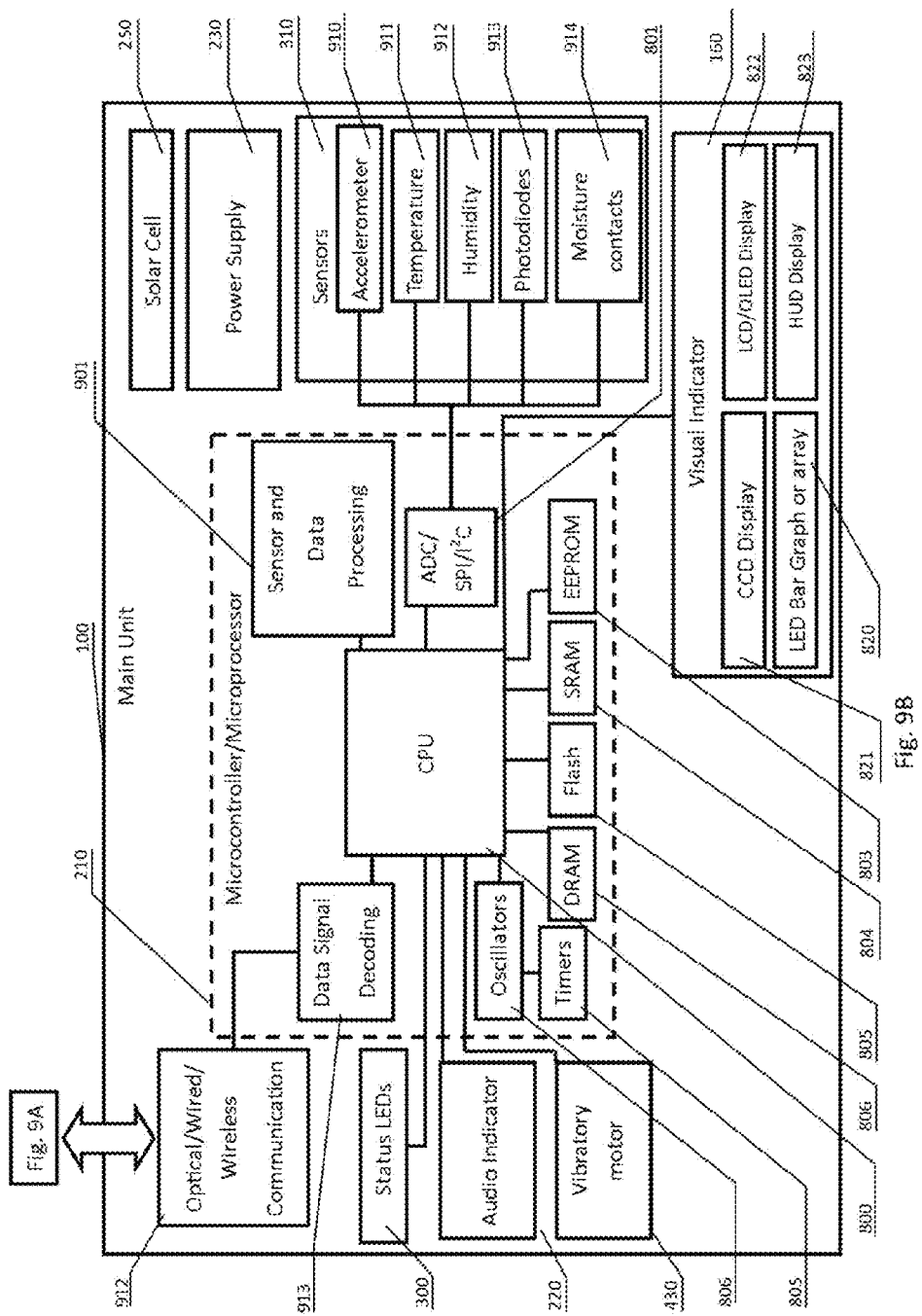

PORTABLE ENVIRONMENT MONITORING AND EARLY WARNING SYSTEM FOR BABIES

PRIORITY STATEMENT

This application claims the non-provisional priority of U.S. Provisional Application No. 61/926,342 filed Jan. 12, 2014, and entitled "Portable Environment Monitoring System for Babies" and also claims the non-provisional priority of U.S. Provisional Application No. 62/062,560 filed Oct. 10, 2014, and entitled "Portable Environment Monitoring and Early Warning System for Babies." Each of these documents is fully incorporated herein by reference for all purposes.

FIELD OF THE DISCLOSURE

The present disclosure relates to maintaining comfort and safety of a baby or small child via a monitoring system possibly integrated with a garment.

SUMMARY

The present disclosure describes an apparatus and method for monitoring the environment of a baby, i.e the outside environment and the direct environment in direct contact with the baby. Environment elements which can be monitored include the temperature, humidity, sunlight intensity and whether or not the environment is damp. Using the temperature and humidity data, the heat index can also be calculated. The child's direct environment is a weighted value which considers the environment elements relating directly to the child and the direct ambient surroundings of the child. This weighted value, for instance, takes into account the skin temperature of the child as well as the ambient temperature, humidity, dampness of the direct surroundings of the child.

New parents are faced with many challenges when having a child. One of these challenges is knowing how to create the best environment for their baby. Every parent is interested in the wellbeing of their child, but for new parents, having no prior experience, issues like the proper bundling or dressing of their baby are difficult to address. This challenge can be minimized by knowing information about that environment, allowing the parent to better react, early enough, before a medical emergency occurs. Such information can include temperature, humidity/dampness and intensity of sunlight their child is exposed to.

One of the most important attributes to monitor is the temperature of the baby's environment. Regulating the temperature of a baby is essential, given that a baby's heat control center is still developing, meaning a baby is unable to regulate their own body to properly react to varying temperatures. This makes a baby more susceptible to hot and cold conditions than that of their caregivers, and varying changes to their environment in general. An adult's body can regulate itself in order to keep comfortable. These regulations can be in form of goose bumps or shivering to help reduce heat loss when it's cold or perspiration in order to cool the body when it's hot. Caregivers may not recognize when a change to a child's environment has occurred and requires immediate attention, as their own body has performed measures to adjust to the changing environment.

Not knowing the temperature of a baby's environment leads to the question of how much, or how little, to bundle or dress a child. Given babies are still developing their heat control centers, it is particularly important to know how much insulation and how much clothing is needed to assure the child isn't too cold, resulting in such medical emergencies as hypothermia or frostbite. At the same time, it is just as important to insure that a child is not overly dressed for particular weather conditions, which can lead to such medical conditions as heat rash, heat cramps and heat exhaustion or medical emergencies like heat stroke.

A further consideration to take into account is the "feels like" temperature, the so-called Heat Index. This calculated value uses the temperature, as well as the relative humidity, in order to calculate a temperature value of how the body perceives a particular temperature [Steadman, 1979]. This can be significantly different than the measured temperature, so-called "dry bulb temperature," given that moisture in the air can cause the human body to perceive the environment to be either substantially warmer or colder than the dry bulb temperature. This value is of great importance when monitoring a baby's environment because, as mentioned previously, a baby's heat control center is still developing and can't react to changes in the environment as well as adults. Given that the heat index considers the temperature in which a human body perceives an environment to be, this offers an even better indicator as to how comfortable the environment is for a baby is exposed to it.

The heat index (HI) which was developed by the National Weather Service, based on the work of [Steadman, 1979], can be calculated using one of three equations which consider the relative humidity (R) percentage value (0-100), and dry bulb temperature (T) in Fahrenheit:

(1) $HI=-42.379+2.04901523T+10.14333127R-0.22475541TR-6.83783\times10-3T^2\times5.481717\times10-2R^2+1.22874\times10-3T^2R+8.5282\times10-4TR^2\times1.99\times10-6T^2R^2$ (2) $HI=0.363445176+0.988622465T+4.777114035R-0.114037667TR-8.50208\times10-4T^2\times2.0716198\times10-2R^2+6.87678\times10-4T^2R+2.74954\times10-4TR^2$ (3) $HI=16.923+0.185212T+5.37941R-0.100254TR+9.41695\times10-3T^2+7.28898\times10-3R^2+3.45372\times10-4T^2R-8.14971\times10-4TR^2+1.02102\times10-5T^2R^2-3.8646\times10-5T^3+2.91583\times10-5R^3+1.42721\times10-6T^3R+1.97483\times10-7TR^3-2.18429\times10-8T^3R^2+8.43296\times10-10T^2R^3-4.81975\times10-11T^3R^3$ [Stull, 2000].

The heat index in Celsius can be then extracted using the standard conversion $T[°\ C.]=(5/9)(T[°\ F.]-32)$.

[Steadman, 1979]—R. G. Steadman, J. Appl. Meteor., 18, 861-873 (1979). [Stull, 2000]—R. Stull, Meteorology for Scientists and Engineers, Second Ed. Brooks/Cole, (2000).

As described above, the measurement of a child's weighted environment can be performed in several ways, described in further detail herein. For example, two ways are described in brief directly below.

1) A measurement resulting from a single sensor located in 1 of 6 orientations relative to child, whereby the weighted environment is directly related to how the sensor is oriented relative to the baby and is influenced by both the baby as well as the ambient environment. This weighted environment can be shifted based on the direction the sensor is placed in relation to baby (namely towards, perpendicular facing up, perpendicular facing down, parallel facing up, parallel facing down and away from baby)

Away from child—Clip on same side as sensor with device tucked into the child's garments (Decided at time of manufacturing due to clip-to-sensor orientation)

Perpendicular facing in or out in relation to the transportation device (assuming a sitting or outward facing child)—Clip on either one of the sides perpendicular to the side the sensor is located on (adjustable by caregiver since clip will be perpendicular to side the sensor is on)

Towards child—clip on opposing side to that of the sensor (decided at time of manufacturing due to Clip to sensor orientation). This allows for the sensor to be in direct contact with the baby or its undergarments/onesie/bodysuit which is direct contact with the baby.

Parallel to baby's body, lengthwise—facing up towards the head or down towards the feet.

2) A measurement resulting from two identical sensors, one of which is facing towards the child, in direct contact with the baby or its undergarments/onesie/bodysuit, ENVIR1, and the other of which is facing out towards the environment, ENVIR2. Whereby the weighted environment is a weighted average of the two sensed data which can then be calculated and presented to the caregiver as the weighted environmental condition. The average of which is calculated as:

$$\text{WeightedENVIR} = x\text{ENVIR1} + (1-x)\text{ENVIR2}; \text{ where } x \text{ is between 0 and 1.}$$

The apparatus described may be designed to assist parents in the early phase of their child's life, particularly for babies under the age of 2 years of age. Monitoring the temperature notifies a parent as to whether or not their baby has been bundled or dressed up too much or too little for the current outside weather conditions. A sensor can also be implemented to warn them if the environment of the child, unbeknownst to the parent, has become damp, as well as if the child is being exposed to too much harmful radiation, like ultraviolet (UV) light.

Embodiments of the apparatus and methods described herein provide for the in situ monitoring of a child's weighted environment while in some mode of transportation, assisting parents and caregivers in guaranteeing the child is transported within the most comfortable environment possible. Most importantly, such a device ensures that the child is not exposed to inappropriate environmental elements which can lead to medical conditions including hypothermia, frostbite, heat rash, heat exhaustion and heat stroke. The device can also help in reducing the number of child hot car deaths because of warnings sent to the caregiver. The device consists of two parts, namely a sensor module and separate main module for processing the data sent from the sensor module. The main module can also be used for measuring the outside environment in order to provide an early warning to changes which will soon affect the child's direct ambient environment. Temporal changes in the child's environment and outside environment are also monitored in order to provide an early warning of rapidly changing environments for the caregiver.

The monitoring and relaying the data relevant to the environment a baby occupies may include: sensor elements for measuring temperature, and/or humidity, and/or dampness, and/or sunlight intensity; a means to relay and process the data, wired or wirelessly, to a main module; a visual indicator or indicators for communicating data to a user; an audible alarm and/or vibrating motor; as well as an internal processor for storing, processing and relaying data. The sensor elements are positioned closely to the baby's midsection in order to properly react to changes in the baby's direct environment which pose a risk. This location is much more effective than say sensors located on a wrist or ankle, as these locations of measurement do not represent immediate risks to the baby's health. For instance, a baby's arm can be cool or cold even if the baby is at no risk because its body is well protected against the elements. A wrist band or ankle band is also impractical based on the size needed to be small enough to be worn by an infant given the size of all the electronic components and battery required. Also, the smaller the device is, the risk of a potential choking hazard is increased.

Additionally, the main module, wherein the data, more specifically the temperature, is indicated to the user, can be clipped to and/or hung from and/or strapped to the carrier/object the baby is being transferred in, (i.e. stroller, car seat, carrier, rucksack, etc.). The main module can also be used for measuring and indicating data collected from the outside environment, more specifically, the environment in which the child's object of transportation is in direct contact with, i.e. outside, inside a house, inside a shopping center, inside a car, etc. The sensor module can relay the data from the child's environment to the main module. Namely, the sensor element, more specifically the temperature probe, is connected to the main module through a wire or fiber optic. In another embodiment the data can be sent from the sensor module wirelessly to the main module via a radio frequency (RF) or optical signal. The data can be sent using one or more transmission techniques including universal asynchronous receiver/transmitter (UART), universal synchronous/asynchronous receiver/transmitter (USART), serial communication and line coding. Wherein line coding can be in the form of but is not limited to Not Return-to-Zero (NRZ) coding, Return-to-Zero (RZ) coding, NRZI (Not-Return-to-Zero Inverted) coding, BiPhase coding, Manchester/Phase Coding, Constant weight coding and Paired-Disparity coding. In order to avoid noise during transmission and receiving of data, the sent data can be preceded by a sync bit or bytes. In order for multiple units to be able to work in the same frequency regime at the same time, without interacting with one another, an address bit or bytes can be used to distinguish individual units and can be sent in the data packet before or after the main set of sensor data.

On the main module the data from the sensor element is displayed by a visual indicator. The outside environment measured at the main module can also be displayed by a visual indicator. Such a visual indicator can be light emitting diodes (LED), and/or LED bar graph or arrays, and/or a liquid crystal display (LCD) and/or a heads up display (HUD), and/or a charge coupled device (CCD) display, and/or an organic light emitting diode (OLED) display. More specific, the visual indicator can be used to represent the temperature through an LED bar graph or array which indicates three temperature and/or heat index ranges for the environment of the baby, namely: too low, normal/OK, and too high as well as two transition regions, namely: warning too low and warning too high. The LED bar graph or array can be with/or without the corresponding numerical temperature indicated next to, or on top of the corresponding LED on the main module. The extreme ranges in temperature and/or heat index on the temperature scale can further be relayed to the caregiver of the baby as a warning through an audible or vibrating alarm. Additionally, improper temperature and/or heat index ranges which have been reached for a predetermined time can also set off an alarm.

Furthermore, the visual indicator can be used to represent the outside temperature and/or heat index within predetermined ranges of too low, OK and too high. Abrupt changes to the outside environment in time are also monitored in order to offer an early warning. These temporal changes can be displayed on the main unit using a visual indicator as well as representing such changes by the blinking frequency of the visual indicator, for instance an LED, used to display the environmental parameter.

In one embodiment, the sensor module uses Bluetooth technology to connect to the main unit, of which could be a cellphone, tablet or computer. On the main unit a program known as an app, can be used to visually display all sensor data from baby's environment. The app can also use weather data from another application or internal sensor in order to determine the outside environmental conditions. The app can connect to the world wide web in order to transmit data of baby's environment to a central database.

BRIEF DESCRIPTION OF THE DRAWINGS

FIG. 9B shows a diagram of the main unit or module making up a system (FIGS. 9A and 9B) for monitoring a complete environment surrounding a baby.

DETAILED DESCRIPTION

Figure 1:
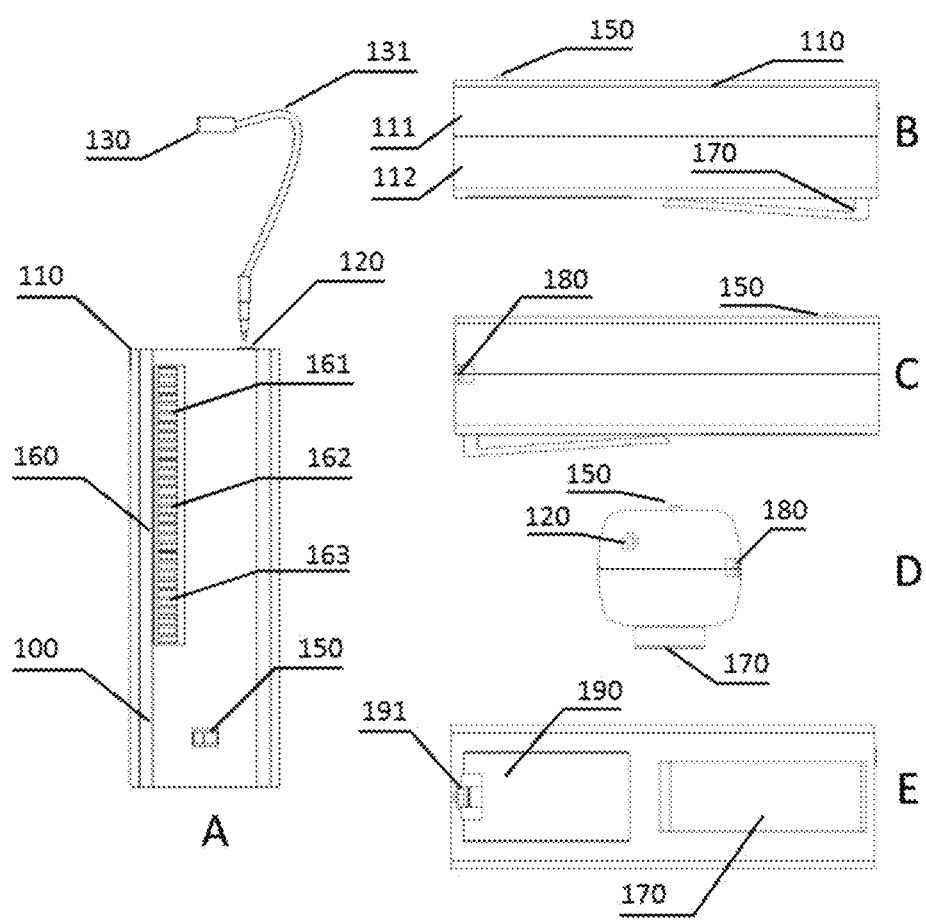
FIG. 1 depicts one embodiment of a main module with accompanied sensor elements connected via wire or optical fiber.

FIG. 1 shows one embodiment of a main unit or module 100 which consists of a main casing 110. In the wired and fiber optic version, a connection port 120 is present for receiving sensor data, via an electric jack or optical sensor, from a sensor element 130. The data can be transmitted from the sensor element through a connecting wire or optical fiber 131. Sensor element 130 may contain numerous sensors for sensing an environment surrounding a baby including, but not limited to: temperature, humidity, heat index, moisture/ dampness, ultraviolet light intensity levels, and visible light intensity levels. For a wireless embodiment of an apparatus, connecting port 120 and connecting wire or fiber optic 131 are omitted and an additional sensor device 500, described below, is required. The main module 100 can be switched off when not in use via a switch 150.

The data relayed from sensor element 130 can be projected, via main module 100 to an end user through a visual indicator 160. Visual indicator 160, as shown in FIG. 1, is comprised of a light emitting diode (LED) bar graph or array, wherein the bar graph or array can be separated into three predetermined ranges. The predetermined ranges in which data can be split into include a range which is too high (red LEDs 161), normal/OK (green LEDs 162), or too low (blue LEDs 163). The range of the sensor data, which can be represented by the LED bar graph or array, can be split into one or more of predetermined ranges.

Additionally FIG. 1 depicts sides B and C as well as a top D view of the main module 100. FIG. 1B also displays that the main casing 110 is composed of two interconnecting parts 111 and 112 which can be screwed or snapped together. Two methods are revealed which can be used for attaching the device to the baby's transportation object. The device can be clipped on via a built-in belt clip 170. Another option is connecting a key ring around a rod 180 built into main casing 110 and then attaching a hooking unit, like a carabineer.

The backside of the main module 100 shown in FIG. 1E reveals a latching cover 190 which can clip 191 to or be screwed to the main module 100 for accessing a battery pack.

Figure 2:
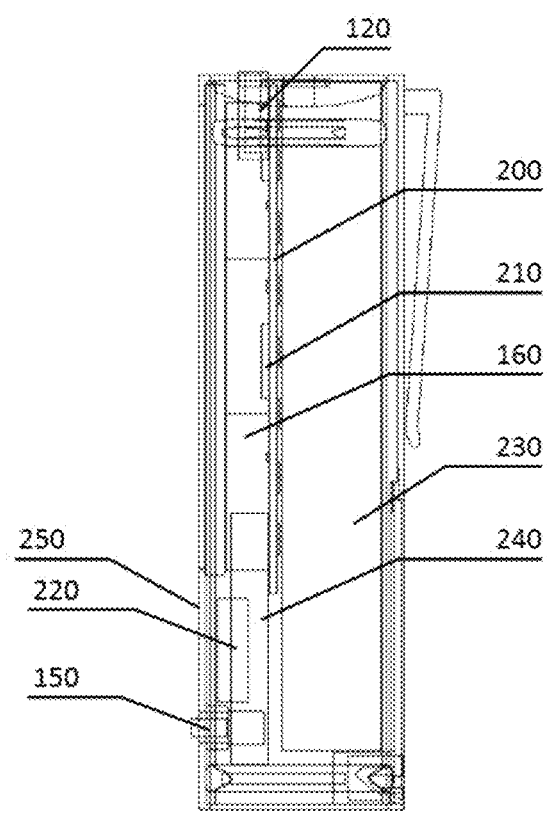
FIG. 2 depicts a side view and internal components of a main module.

FIG. 2 shows an internal view of main module 100 revealing a PCB board 200 on which the circuitry is soldered to metal leads for interconnecting all components. One component is a microcontroller 210 for managing the whole system and storing a program for managing the sensor data, performing calculations and transmitting/receiving data. The circuitry is comprised of typical electronic components, capacitors, resistors, etc. required for general operation, but also includes distinctive electrical components. These distinctive components include a visual indicator 160 and an audible piezo 220. The audible piezo is for alerting when predetermined ranges of the sensed environment are reached or if a non-ideal range has been maintained for a predetermined amount of time. The circuit is powered by a battery pack 230. For the wireless version of the apparatus, an RF or optical receiver 240 can be mounted for collecting the transmitted data from the temperature sensor. A solar cell 250 can also be mounted for providing a continued trickle charge for the battery pack 230.

The visual indicator 160 can be one or more of the following: an LED bar graph or array, a liquid crystal display (LCD), an organic light emitting diode (OLED) display, or a charge coupled device (CCD) display.

FIG. 3A reveals an alternative embodiment of main module 100, which is more compact and offers a number of additional options and components. For one, an indication LED 300 can be used for indicating that data from sensor unit 500 was received by main module 100. The top section 111 and bottom section 112 of the main casing 110 can be screwed together via screw holes 340. The visual indicator 160 can be split up further into more detailed indicator regions namely, too high (red LEDs 161), warning becoming too high (yellow LEDs 161'), normal/OK (green LEDs 162), warning becoming too low (yellow LEDs 163'), or too low (blue LEDs 163). The outside environmental sensors 310 can measure environmental factors relating to the environment in direct contact with the transportation device 700 the child is being transported in. This data can be visually displayed in an additional visual indicator, here a set of three LEDs to represent too high (a red LED 311), normal/OK (a green LED 312), or too low (a blue LED 313).

Figure 3:
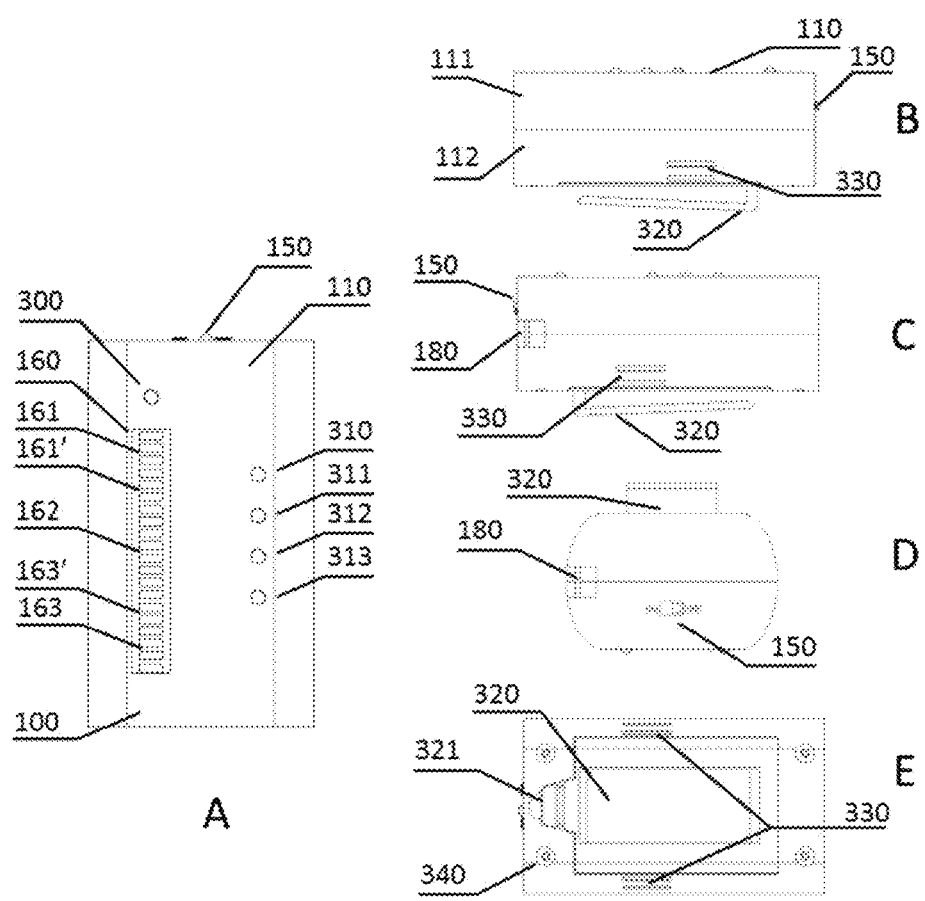
FIG. 3 depicts a second embodiment of a main module with visual indicators for the baby's and outside environment.

Also shown in FIG. 3 are sides B and C as well as a top D view and backside E of the main module 100. A latching battery cover 320 consists of a battery cover 190 with a belt clip 170 built in, which is secured to the main module 100 either by a releasable latch 321 or screw. The main module 100 can be secured to transportation device 700 using a hook-and-loop fastener strap which is laced through slots 330.

Figure 4:
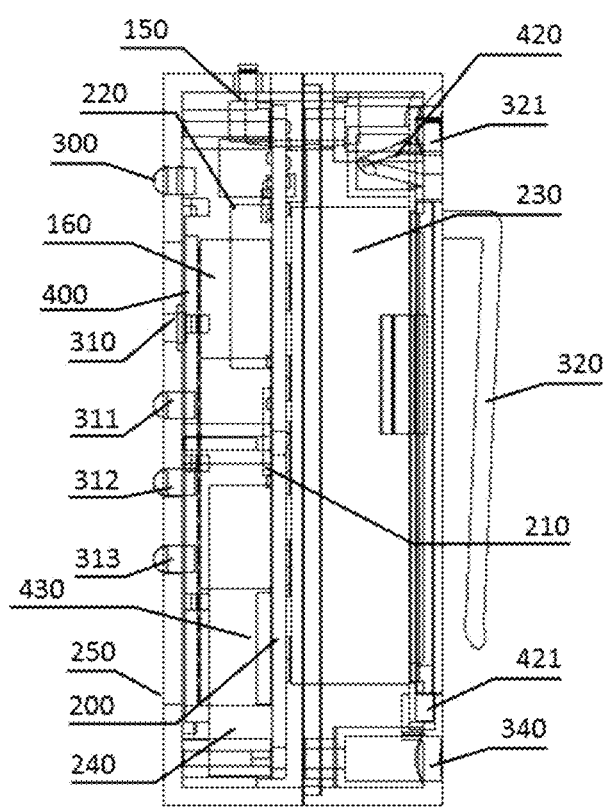
FIG. 4 depicts the side view of the second embodiment of a main module revealing the internal components.

FIG. 4 shows an internal view of the alternative embodiment of main unit or module 100 revealing a transparent window 400 for separating the visual indicator 160 from the outside environment. The battery cover 320 can be secured to the main body 110 by sliding tabs 421 on one side into the bottom section 112. The other side of the battery cover 320 snaps into the bottom section and is held secure with a releasable button 321 which can unlatch a tab 420. The audible alarm 220 or a vibration motor 430 can be used for alerting the caregiver of warning or alarm conditions based on the outside or baby's environment.

Figure 5:
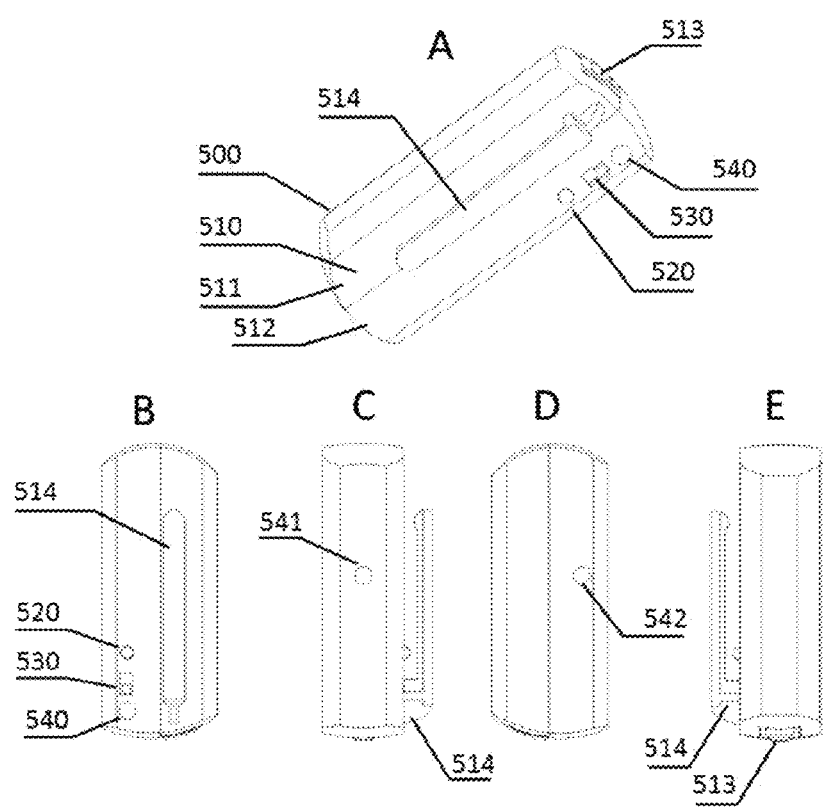
FIG. 5 depicts the side and perspective view of an environment sensor module which is placed next to a baby.

FIG. 5 shows one embodiment for a wireless apparatus embodiment which requires an additional sensor unit or module 500 for measuring and transmitting the sensed data of the environment surrounding a baby. The figure illustrates a perspective view A of sensor unit or module 500 as well as a side views B, C, D and E. The sensor module comprises a casing 510 for enclosing the electronics and sensor elements 130. The casing 510 is made up of two parts, a bottom section 512 which contains the electronics and the top section 511 which covers the battery and snaps into or screws to the bottom section 512. The release button 513 allows the battery cover 511 to be removed from the main bottom casing 512. The wireless sensor module 500 has an LED 520 for indicating the status of data transmission. The module can be turned off when not in use by a switch 530. The module can have a clip 514 which can be used for securing the module to the clothing of the baby or the bundles of blanket the child is wrapped in. This allows for placement of the unit to sit between the undergarments, or onesie/bodysuit, of the baby and the rest of the baby's garments and/or bundles of blanket.

The sensor module is positioned in such a way where, when clipped to the pants of a baby, the sensor unit 500 is placed on the inside of the pants, in between the baby and the pants. The weighted environment of the child can be either measured as a weighted average of the baby's direct environment measured by sensor 540 and the baby's skin/core temperature measured by sensor 542, which is in direct contact with the baby or the baby's undergarments/onesie/bodysuit. Or the weighted environment can be measured from a single sensor 541 which measures the weighted environment which is influenced by both the baby's skin/core temperature as well as the baby's direct environment, based on the location of the sensor, namely parallel to baby, more specifically not aimed directly at child nor directly out towards the child's direct environment.

Figure 6:
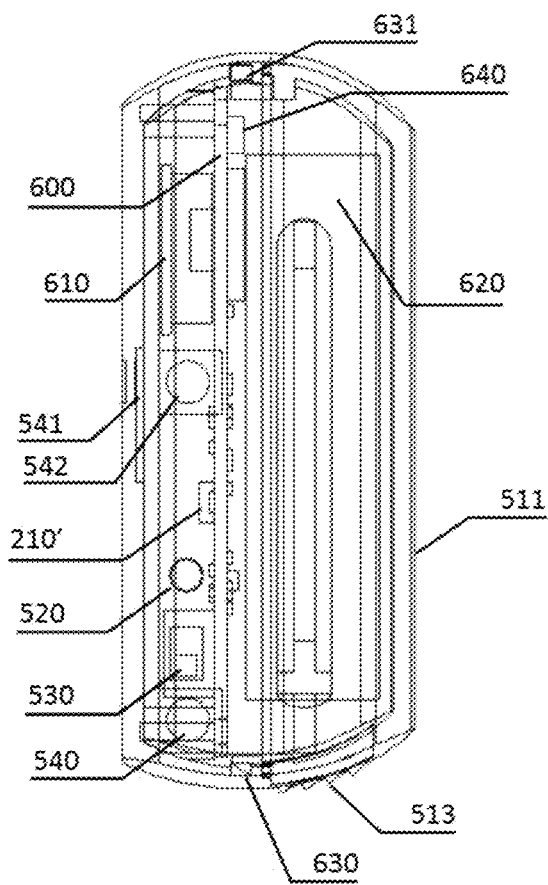
FIG. 6 depicts a side view and internal components of an environment sensor module which is placed next to a baby.

FIG. 6 shows a side view of the internal components of sensor module 500. Sensor module 500 has a PCB board 600 which all electrical components are soldered to, interconnecting them. A microcontroller 210' is needed for interpreting, calculating and transmitting/receiving the data from the sensor elements 130, at sensor locations 540, 541 and 542, of which are able to measure any of a number of aspects of a baby's environment as mentioned above. Sensor module 500 has an RF or optical transmitter 610 and the whole system is battery powered 620. The battery cover 511 can be secured to the bottom section 512, by sliding tabs 631 on the battery cover 511 into the bottom casing 512, snapping them together. By pressing the release button 513, a tab 630 is pushed in, allowing for the battery cover 511 to be removed from the bottom unit 512. If two sensors are used to determine the weighted environment of the baby, namely 542 and 540, the weighting factor can be either preset at time of manufacturing or it can be selected by the caregiver using a tuning knob/switch 640 for adjusting the weighting factor to one of a set of predetermined ratios.

Figure 7:
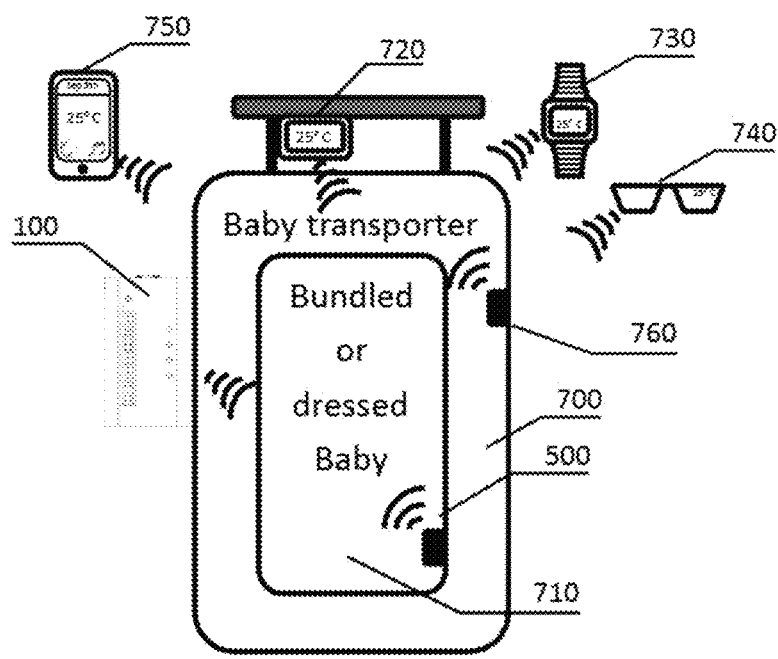
FIG. 7 depicts an environment sensor module placed next to a baby, which relays measured data to any of a number of main units handled by a caretaker while the baby is in an object designed for transportation.

FIG. 7 illustrates the relative location of an apparatus with respect to a child's transportation vehicle 700, i.e. baby carriage/stroller/carrier/rucksack. This includes sensor module 500 placed within bundles or clothing 710 a baby is wrapped in or wearing, which measures an environment a baby occupies. Any number of devices can be used to interpret the transmitted data from sensor module 500 and relay data to the end user. Potential receiving units include any of the following main component or sub-component of an independent or integrated device: A main module 100 as mentioned above; a stroller apparatus 720 built in as part of the transportation vehicle 700; a watch or wristband 730; a pair of glasses or headware 740; and a cellphone 750. An additional outside environmental sensor device 760 can also collect data pertaining to the outside environment, and relay such data to the main module 100, a watch/wristband 730; a pair of glasses 740; or a cellphone 750.

Figure 8:
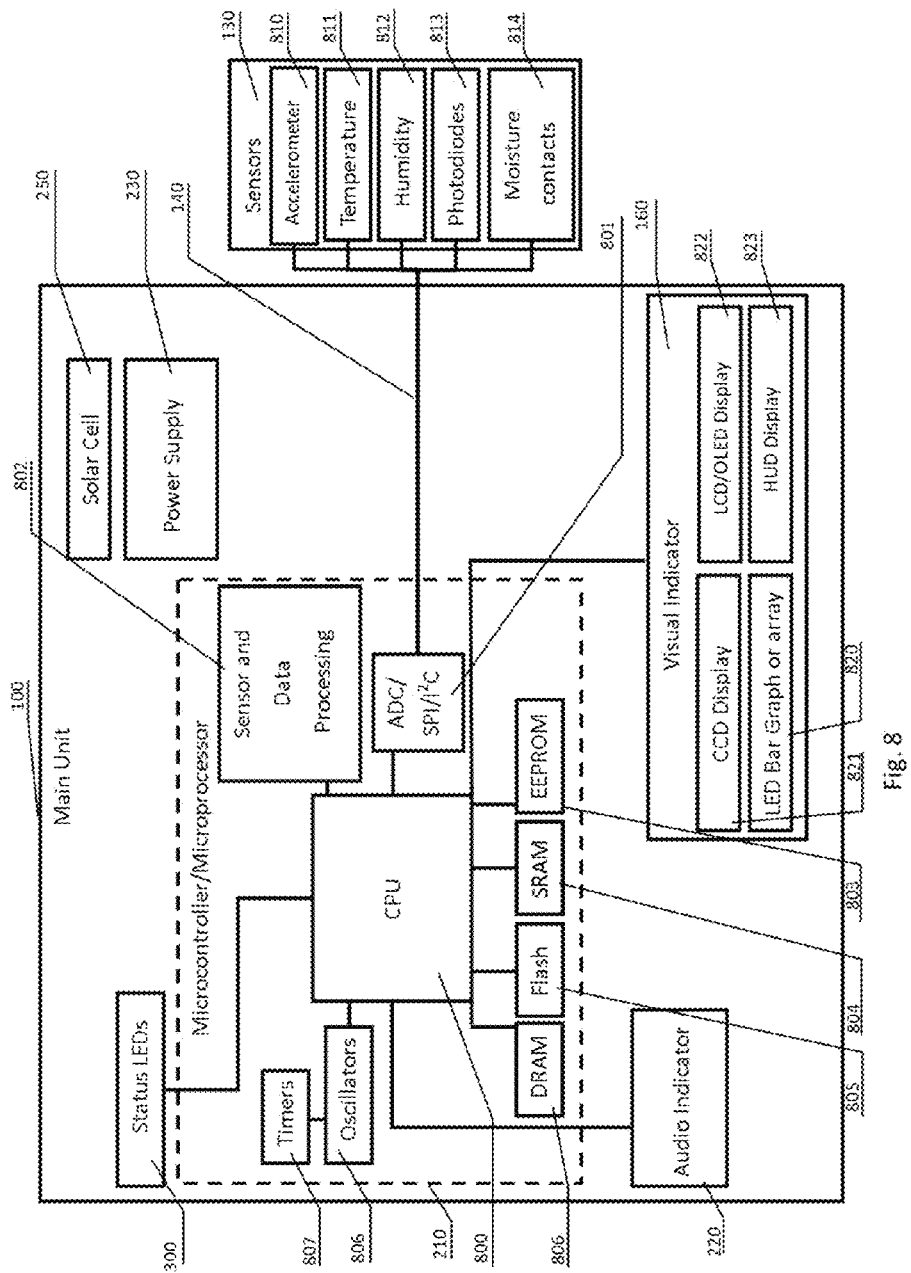
FIG. 8 shows one embodiment with a single or main unit wired to sensors monitoring a complete environment surrounding a baby.

FIG. 8 shows a system diagram for the organization of main unit 100 which is connected directly to sensor element 130, through a wire or optical fiber 140 and whose data is processed by the microcontroller using analog to digital converter (ADC), Serial Peripheral Interface Bus (SPI) or Inter-Integrated Circuit ($I^2C$) methods 801. Sensor element 130 can comprise numerous individual sensors for measuring acceleration 810, temperature 811, humidity 812, light intensity 813 and moisture 814. A microcontroller 210 receives the sensor data directly from sensor element 130. Microcontroller 210 then processes the data 802, performing necessary calculations using the central processing unit (CPU) 800, and can present it to the end user through an audible alarm 220 and displays it onto a visual indicator 160. Visual indicator 160 can be any or all of the following: an LED bar graph or array 820; a CCD display 821; an LCD/OLED display 822; or a HUD display 823. An audio indicator 220 can also be used for indicating to the user that certain functions performed by the microcontroller 210 have been performed or to indicate numerous alarm or warning conditions.

The microcontroller 210 performs actions based on predetermined timings using timers 807 which are determined and kept accurate by internal or external oscillators 806. The program, variables, data and device history can be stored in different memory locations including electrically erasable programmable read-only memory (EEPROM) 803, static random-access memory (SRAM) 804, flash memory 805 or dynamic random-access memory (DRAM) 806 which can be internal or external to the microcontroller 210. Status LEDs 300 can be used for different purposes including being used to inform that data has been received and/or processed.

Figure 9A:
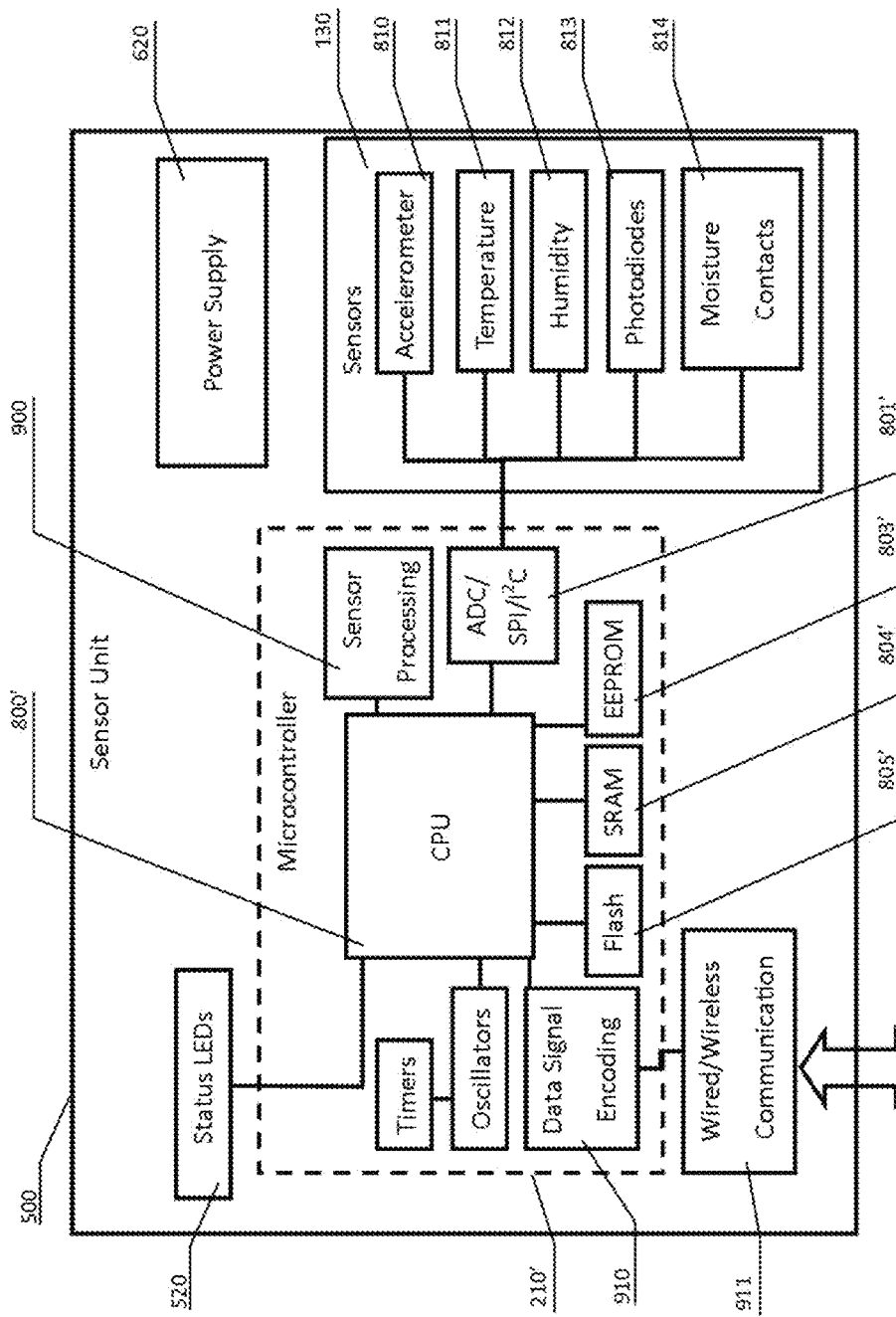
FIG. 9A shows another embodiment with a sensor unit or module with a wireless connection to a main unit or module completing a system for monitoring a complete environment surrounding a baby.

FIGS. 9A and 9B show a system diagram for the two-module embodiment. The layout is very similar to that presented in FIG. 8. However, there is no physical connection from the sensor element 130 to the visual indicator 160. Instead, two independent units are required, a main unit or module 100 and a sensor unit or module 500. FIG. 9A depicts sensor module 500 which collects the environmental data from sensor element 130 and sensor processing 900 is performed by a microcontroller 210'. The data is encoded 910 and is transmitted to the main module 100 using an RF or optical transmitter 610. The main module 100, depicted in FIG. 9B, then receives the signal using an RF or optical receiver 912. The signal is then decoded 913 and processed 901. A microcontroller 210 then processes the signal and presents it to the end user through an audible alarm 220 and/or vibrational motor 430 and displays it onto a visual indicator 160. The visual indicator 160 can be any or all of the following: an LED bar graph or array 820; a CCD display 821; an LCD/OLED display 822; or a HUD display 823. The outside environment can be measured using sensors 310 on the main unit 100. Sensors can be used for measuring acceleration 910, temperature 911, humidity 912, light intensity 913 or moisture 914. This data is processed 901 by the microcontroller 210 and displayed on a visual indicator 311-313.

Figure 10:
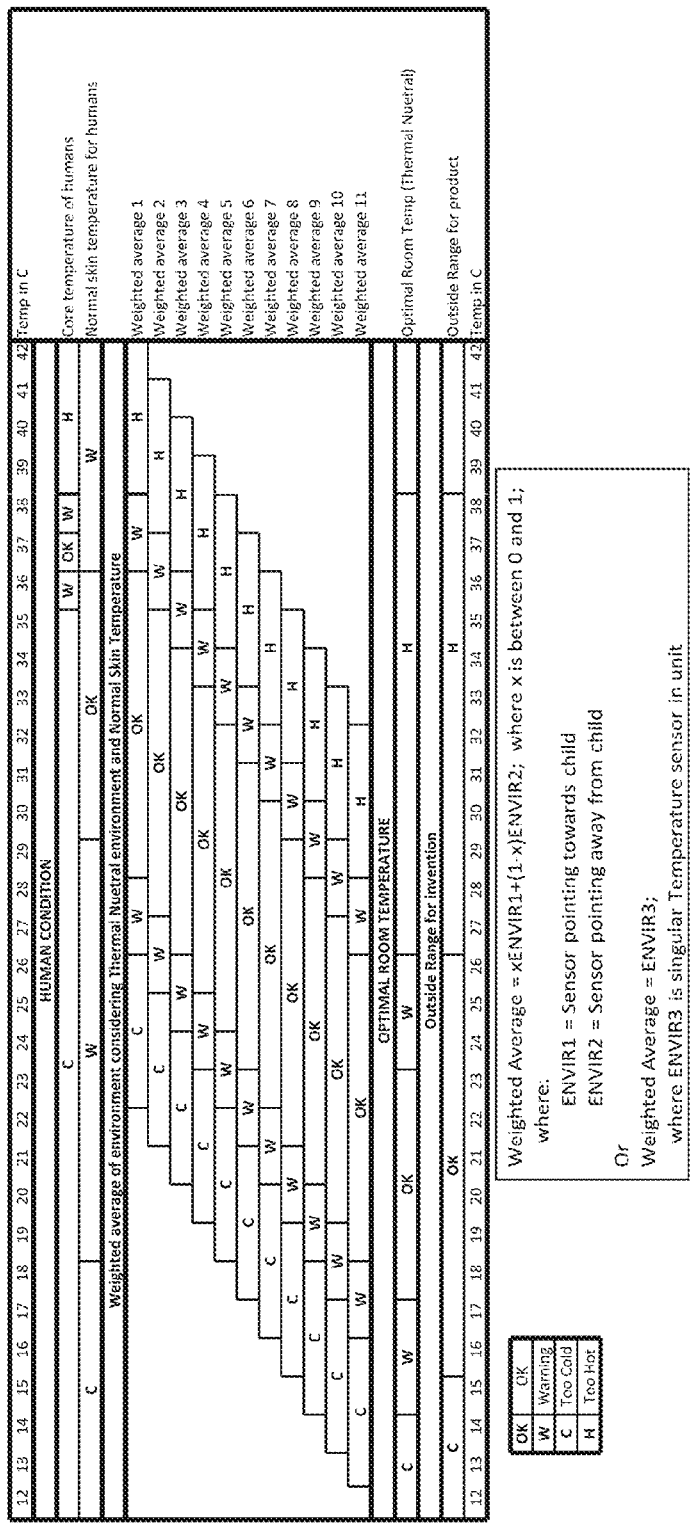
FIG. 10 depicts different temperature ranges of different relevant systems.

FIG. 10 depicts different temperature ranges of relevant different systems including the core temperature of humans 1000 and the normal skin temperature range of humans 1001. Also included are: An example of the movable scale of ranges of the weighted average of a baby's environment (the ranges of which can be smaller or larger than shown here) which can be used 1010; the range of thermal neutrality 1020, also known as room temperature; and one embodiment of the outside temperature range 1030. The core temperature of a human 1000 should be 37° C. Plus or minus 1° C. from the optimal 37° C. is considered a range of warning where the body has started to become too cold or too hot. For ranges which lie greater or less than 2° C. it is considered too hot or too cold, is dangerous and can become life threatening. The range of the normal skin temperature of a human 1001 is much larger. The skin has thermoreceptors which, in an adult, are active for detecting both warmth and coldness to act as a warning system. In the OK skin temperature range, both of these types of thermoreceptors are active. As the temperature increases or decreases, the thermoreceptors for detecting heat or cold become more or less active, depending on the temperature. These allow the body to react to non-optimal conditions by, for instance sweating if it's too hot or shivering if it's too cold. Within the warning ranges, these thermoreceptors are most active. As the skin temperature becomes too cold or too hot, the thermoreceptors will result in creating a pain sensation for the body and eventually go numb if the temperature is too extreme. Optimal room temperature 1020 is determined by a temperature range in where the human body feels thermally neutral.

The ranges in which the weighted average of the baby's environment 1010 that is measured are chosen on a movable scale which lies between the normal skin temperature of a human 1001 and the outside environment when in a thermal neutral range 1020. The deciding factor on how close the scale of the weighted average is to that of the normal skin temperature 1001 and room temperature 1020 is based on how much the ambient temperature of the baby's environment is considered in the calculation 1010' versus the baby's skin/core temperature. If the baby's skin/core temperature is weighted more, the scale is placed closer to the normal skin temperature of humans 1001. Whereas if the ambient temperature of the baby's environment is weighted higher, the scale can be shifted down closer to the optimal room temperature range 1020. The ranges of the weighted average of the environment of the baby 1010 can be split up into five different ranges including too cold 163, warning of becoming too cold 163', OK 162, warning of becoming too hot 161' and too hot 161.

One example of the OK range 312 of the outside range 1030 is chosen to be centered on the thermal neutral range of humans 1020, as this is considered a range in which humans are within an optimal temperature zone. The too hot range 311, or the too cold range 313 are placed in regions outside of this thermal neutral zone 1020, as these are marginal ranges in which a person will have to compensate by wearing more or less clothing in order to stay safe and comfortable.

Figure 11:
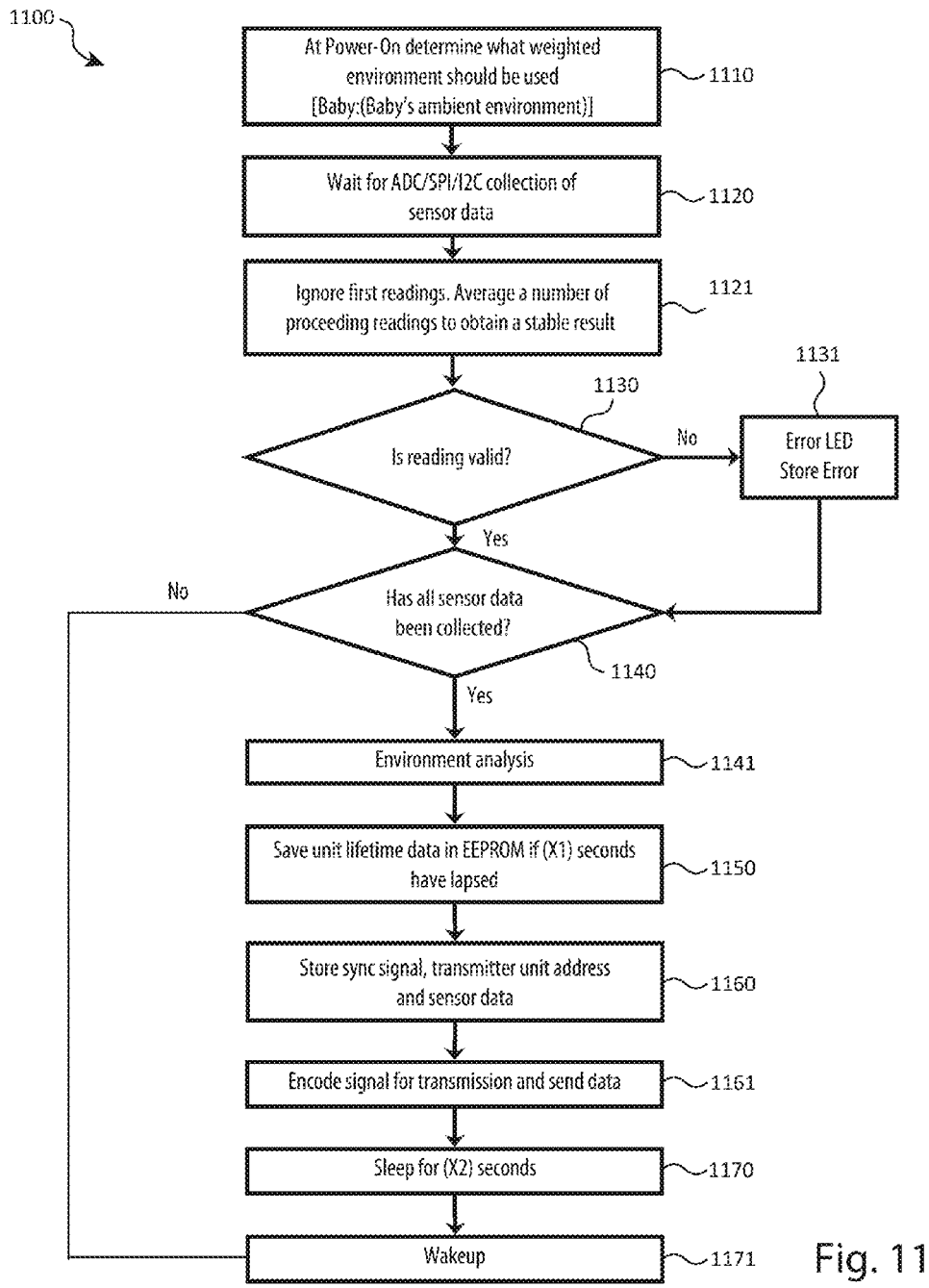
FIG. 11 shows the flow of operations performed by the sensor module of FIG. 9A.

FIG. 11 shows an operations flowchart 1100 according to one embodiment. The operation flow may be performed by hard wired logic or by a program-controlled microcontroller 210' within the sensor module 500. Accordingly, the "operations" referred to herein may be performed as process steps by hard wired logic, an intelligent electronic chip or module, or any combination of both. At power-on, operation 1110 loads the weighting factor to be used by environment analysis operation 1141 when determining the baby's weighted environment. This weighting factor can be preset in the sensor module or setup by the parent for loading into the sensor module. Data collect operation 1120 waits for the sensor data via an ADC, SPI or I²C signal 1110 from one or more sensors in sensor unit 130. Averaging operation 1121 can ignore the first few readings and average the following readings in order to obtain a stable result. This data is then converted into the appropriate units of the measurement (i.e. degrees Celsius or Fahrenheit for temperature). Test operation 1130 detects if the reading is valid, for example within an expected range. If the reading is not valid, the operation flow branches NO to error marking operation 1131 where an LED is turned on and the error stored in memory. If the reading is valid, the operation flow branches YES to test operation 1140. Test operation 1140 detects if all sensor data has been collected. If not, the operation flow returns back to data collect operation 1120. If all sensor data has been collected, the operation flow branches YES to environment analysis operation 1141. This operation uses the weighting factor to combine the baby's core sensed data with the baby's ambient sensed data. When X1 number of minutes have lapsed since the last lifetime update, save data operations stores the unit lifetime data into the internal or external EEPROM.

The sync store operation 1160 then stores a sync signal, for synching to the receiver unit, the unit's personal address, in order to have multiple units working side-by-side without cross-talk, and the sensor data. Send data operation 1161 encodes data signals using one of, but not limited to, the following methods: Not-Return-to-Zero (NRZ) coding, Return-to-Zero (RZ) coding, Not-Return-to-Zero-Inverted (NRZI) coding, BiPhase coding, Manchester (Phase) coding, Constant-Weight coding, or Paired Disparity coding. The encoded signal is then transmitted 1161 using UART, USART or serial communication transmissions techniques. The sensor unit then goes to sleep at operation 1170 for X2 seconds in order to save energy, and is woken back up at operation 1171 to start the sensor module process 1100 all over again.

Figure 12A:
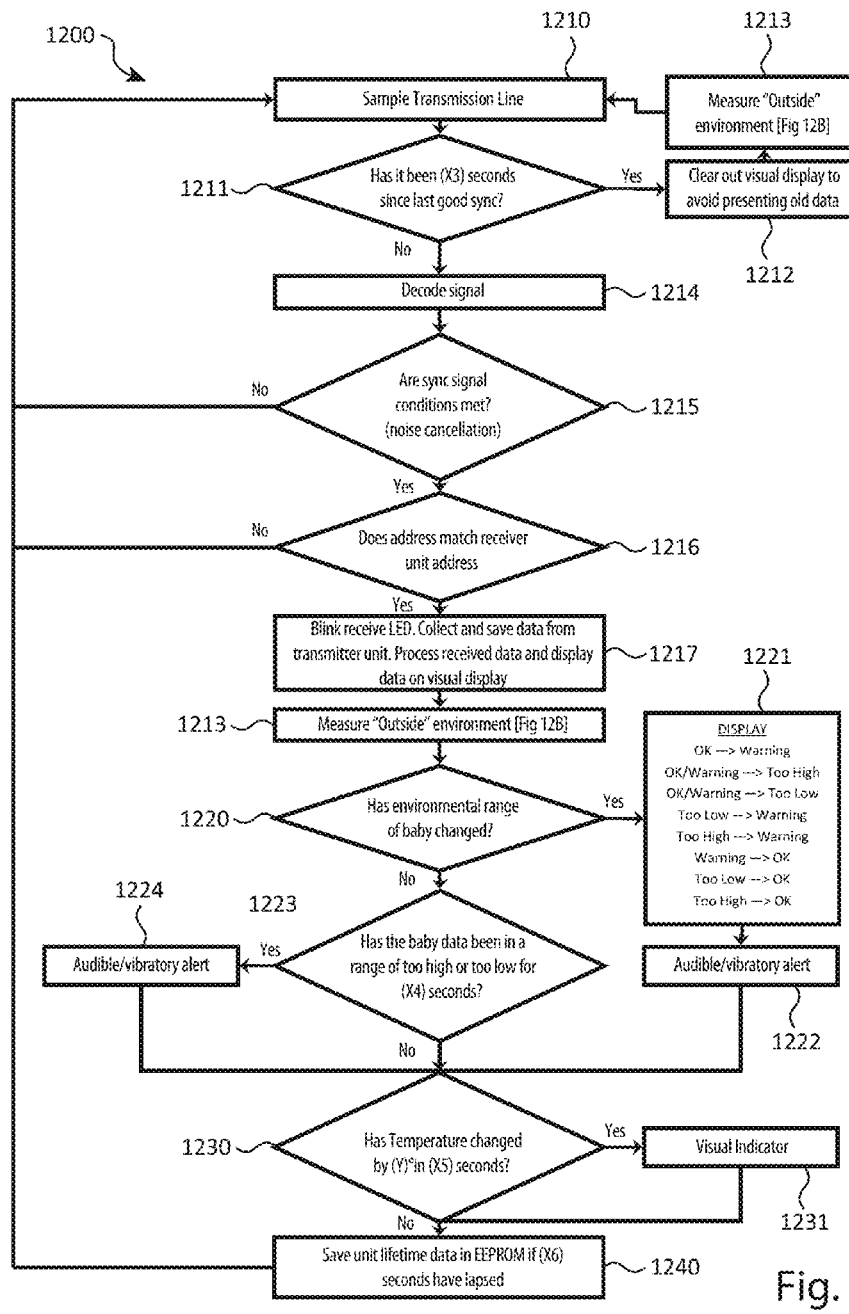
FIG. 12A shows the flow of operations performed by the main module of FIG. 9B.

FIG. 12A shows the flow of operations 1200 performed by the main unit or module 100 (FIG. 9B) to process data from the sensor unit or module 500 (FIG. 9A) to issue warnings and display monitoring results. The operation flow 1200 begins with sample operation 1210 sampling the transmission line 1210 sampling the data signal from the sensor unit 500 and the outside environment data from measure-outsideenvironment operation 1213. Test operation 1211 detects whether it has been more than X3 seconds since the last successful received data. If it has been more than X3 seconds, the operation flow branches YES to clear display operation 1212. If not, the operation flow branches NO to decode operation 1214. Clear display operation clears the visual display is either cleared 1212 (in case LEDs are used to represent the data) or a notification is displayed (if a display unit like a CCD, etc is used). This assures that the caregiver does not have old data presented to them, giving them false information. Measure outside environment operation 1213 measures the outside environment from sensors in the main unit and updates the outside environment display in the main unit 100. Measure operation 1213 is described hereinafter with reference to FIG. 12B.

In FIG. 12A, if less than X3 seconds has gone by since the last sync, decode operation 1214 receives signal data from sensor unit 500 as sampled by the sampling operation 1210 and decodes it. Sync detect operation 1215 detects if the sync is successful. If sync is detected, operation flow branches YES to address test operation 1216. If sync is not detected, the operation flow returns to sampling operation 1210. Address test operation 1216 detects whether the received address matches the internal address of the main unit 100. If these addresses match, the operation flow branches YES to process signal data operation 1217. Process signal data operation sets a received data notification to be displayed to the user, saves the received signal data, and processes the signal data for display to the caregiver on the visual display in main unit 100. The outside environment is then measured in measure operation 1213 and displayed as hereinafter described in reference to FIG. 12B. Detect operation 1220 then checks to see if the range of the baby's environment has changed since the last measurement. If the range has changed, the operation flow branches to warning operation 1221. The warning operation displays a visual warning, and alert operation 1222 generates an audible alert or vibratory alert. If the range has not changed, the operation flow branches NO to High/Low test operation 1223. High/Low test operation detects whether the baby data environment has been too low or too high for X4 seconds. If it has been, there environmental conditions that could be hazardous to the baby, and the operation flow branches YES to alert operation 1224 which generates an additional audible or vibratory alert. If the baby's environment has not been too low or too high for X4 seconds, the operation flow branches NO to large change detect operation 1230. The large change detect operation tests whether the temperature or heat index of the baby's environment or outside environment has changed by Y° in X5 seconds. If there has been significant change, the operation flow branches YES to warning operation 1231 which would indicate a warning that can be displayed to the caregiver as a visual indicator. If there is no large change, the operation flow branches NO to save operation 1240 to store history of the data on the EEPROM every X6 seconds.

Figure 12B:
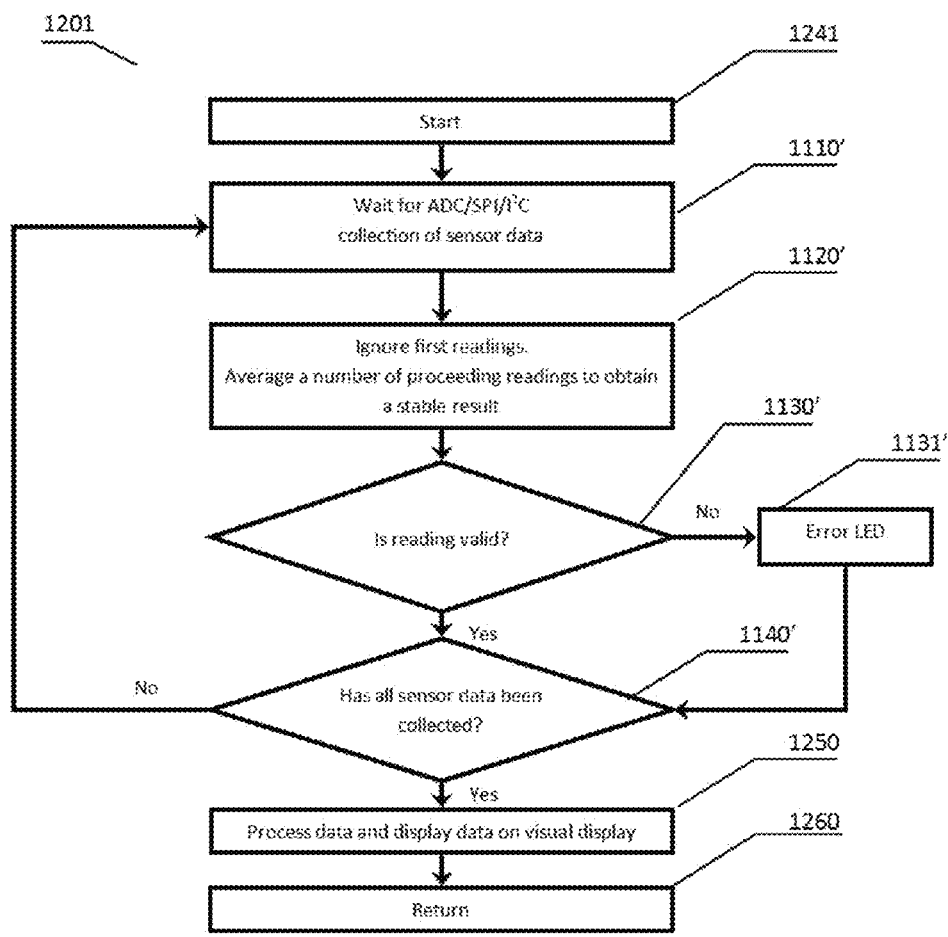
FIG. 12B shows the operational flow for the measures-outside-environment operation 1213 within the main module of FIG. 12 B.

FIG. 12B shows a flow of operations performed by the measure-outside-environment operation 1213 (FIG. 12A). When the operation flow starts 1241, data collect operation 1110' waits for the data from sensors for outside environment received via an ADC, SPI or I²C signal from the outside environment sensor unit 310 (FIG. 9B). Averaging operation 1120' can ignore the first few readings and average the following readings in order to obtain a stable result. This data is then converted into the appropriate units of the measurement (i.e. degrees Celsius or Fahrenheit for temperature). Test operation 1130' detects if the reading is valid, for example within an expected range. If the reading is not valid, the operation flow branches NO to error marking operation 1131' where an LED can be turned on and the error stored in memory. If the reading is valid, the operation flow branches YES to test operation 1140'. Test operation 1140' detects if all sensor data has been collected. If not, the operation flow returns back to data collect operation 1110'. If all sensor data has been collected, the operation flow branches YES to process outside environment data operation 1250 for visual display to the caregiver, in one embodiment, with LEDs indicating that the outside environment is too low 313, OK 312, or too high 311. The operation flow then returns 1260 to the main flow 1200 from where it left off.

Figure 13A:
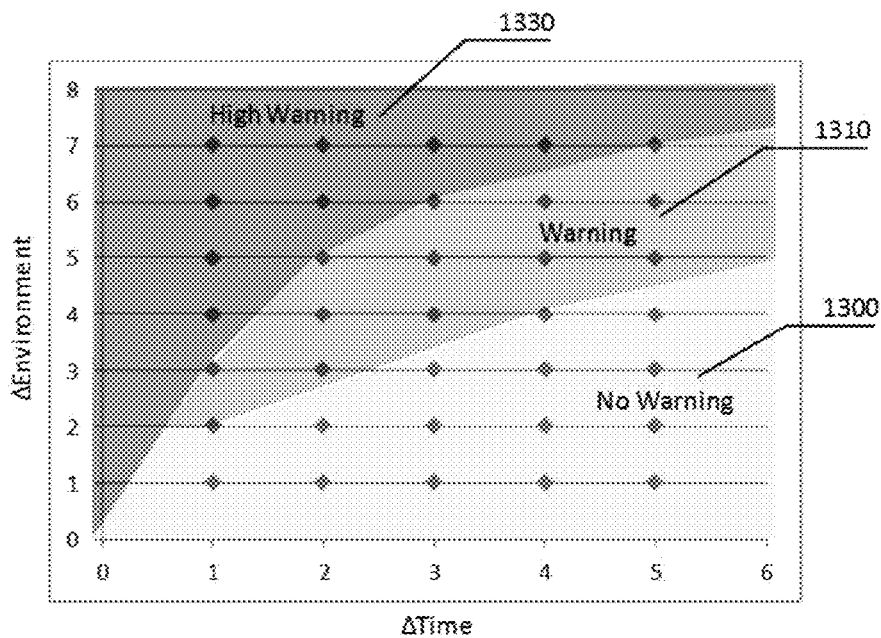
FIG. 13A depicts a graph of ΔEnvironment vs. ΔTime for determining different warning regions based on temporal changes in the environment.
Figure 13B:
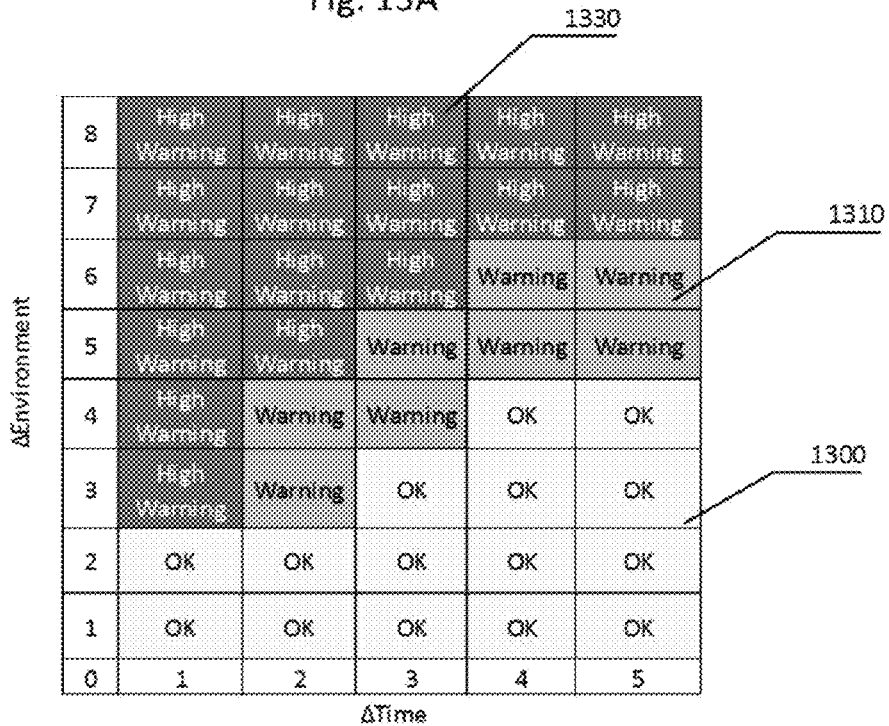
FIG. 13B depicts a table of ΔEnvironment vs. ΔTime for determining different warning regions based on temporal changes in the environment.

The main module can also check for changes in the environment within a given time 1230 as described earlier. This is visually explained in FIG. 13 as a graph FIG. 13A and a table FIG. 13B. If there is a quick change in the environment in a short amount of time it is considered a high warning 1330 and can be displayed as a visual indicator to the caregiver. This high warning region 1330 is treated as such because recognizing quick changes in, for instance, the outside environment can serve as an early warning to the caregiver that the condition of the baby's environment, although previously ok, can change rapidly if precautionary changes aren't made, i.e. adding or removing additional layers to the baby. For slower changes in the environmental conditions there exists a warning range 1310 to let the caregiver know that attention should be given soon, in order for the child's environment to remain OK. For even slower changes in the environment it is considered as a no warning range 1300.

While this disclosure has described the invention by reference to the above preferred embodiments and priority applications, it will be appreciated by one skilled in the art that the invention may be implemented in various other embodiments without departing from the spirit and scope of the invention.

What is claimed is:

1. An apparatus for monitoring a multilayered baby environment surrounding a baby where the multilayered environment includes core environmental elements in direct contact with the body of the baby, ambient environmental elements within a layer of garments providing an ambient environment between the baby and outside environmental elements outside the layer of garments, said apparatus comprising:
   a sensor module with multiple sensors distributed in the multilayered environment for sensing environmental elements in each layer;
   an ambient analysis module for combining the sensor data from sensors in the core layer and in the ambient layer to produce combined ambient environmental data;
   a display module for displaying said combined ambient and core environmental data indicative of a complete ambient environment surrounding the baby in the multilayered environment and thereby provide proactive information for care of the baby;
   a transmitting module for sending said combined ambient environmental data from the sensor module to a main module;
   an outside environment module in the main module having one or more outside environment sensors for sensing the outside environmental elements, and having a detect module for detecting at least one changing of the outside environmental elements;
   the display module being in the main module, and adapted to be responsive to the at least one changing of the outside environmental elements, and for providing proactive information for care of the baby;

wherein the outside environment sensors are for sensing the one or more outside environmental elements selected from the group consisting of temperature, humidity, moisture/dampness, ultraviolet light intensity levels, and visible light intensity levels of an outside environment of the baby; and wherein said ambient analysis module further comprises an ambient environmental weighted combination module for:

combining ambient environmental data from the one or more ambient environmental elements of an ambient environment of the baby with core environmental data from one or more of the baby's core environmental elements;

wherein the combining ambient environmental data and core environmental data includes weighting the ambient environmental data with a first weighting factor and weighting the core environmental data with a second weighting factor.

2. The apparatus of claim 1, wherein said display module comprises:

a warning module displaying ranges of combined environmental data indicating when the environmental conditions are normal and hazardous for the baby; and an alert module responsive to hazardous environmental conditions generating one or more alarms selected from the group consisting of: visual, audible and vibratory.

3. The apparatus of claim 1, wherein said multiple sensors distributed in the multilayered environment in the sensor module comprise one or more sensors for sensing one or more environmental elements selected from the group consisting of: temperature, humidity, moisture/dampness, ultraviolet light intensity levels, and visible light intensity levels of said ambient environment of the baby.

* * * * *